United States Patent
Mick et al.

(10) Patent No.: US 6,579,262 B1
(45) Date of Patent: Jun. 17, 2003

(54) BRACHYTHERAPY NEEDLE IMPLANTATION TEMPLATE

(75) Inventors: Felix W. Mick, Bronxville, NY (US); Kenneth Zabrouski, Bethpage, NY (US)

(73) Assignee: Mick Radio-Nuclear Instruments, Inc., Mount Vernon, NY (US)

( * ) Notice: Subject to any disclaimer, the term of this patent is extended or adjusted under 35 U.S.C. 154(b) by 0 days.

(21) Appl. No.: 09/490,832

(22) Filed: Jan. 25, 2000

(51) Int. Cl.$^7$ .............................................. A61M 5/00
(52) U.S. Cl. ...................................... 604/116; 604/117
(58) Field of Search ............................. 604/116, 48, 57, 604/60, 117, 174; 600/1–8, 459; 606/108, 130; 424/1.4, 1.33

(56) References Cited

U.S. PATENT DOCUMENTS

| | | | |
|---|---|---|---|
| 4,402,308 A | | 9/1983 | Scott |
| 4,427,005 A | * | 1/1984 | Tener .................... 128/DIG. 6 |
| 4,580,561 A | * | 4/1986 | Williamson ................ 128/898 |
| 4,642,096 A | * | 2/1987 | Katz ..................... 128/DIG. 6 |
| 4,754,745 A | | 7/1988 | Horowitz |
| 4,759,345 A | | 7/1988 | Mistry |
| 4,798,212 A | * | 1/1989 | Arana ........................ 600/562 |
| 4,881,938 A | | 11/1989 | van't Hooft |
| 5,562,594 A | | 10/1996 | Weeks |
| 5,626,829 A | | 5/1997 | Koutrouvelis |
| 5,868,757 A | | 2/1999 | Koutrouvelis |
| 5,871,448 A | | 2/1999 | Ellard |
| 5,938,583 A | | 8/1999 | Grimm |
| 6,036,632 A | * | 3/2000 | Whitmore et al. ............. 600/7 |

FOREIGN PATENT DOCUMENTS

EP 158630 4/1985

OTHER PUBLICATIONS

Jacobson, et. al., Hematology/Oncology Clinics of North America, Prostate Cancer, Jun. 1996, 653–673.

Balter, et. al.., International Journal of Radiation Oncology Biology Physics, Dec. 1, 1995, 1281–1286.

Marinelli, et. al., The Journal of Urology, Mar. 1992, 922–925.

Brosman, et. al., Urology, Oct. 1991, 372–376.

Kumar, et al., Journal of the National Medical Association, 1990, 181–193.

Martinez, et. al., International Journal of Radiation Oncology Biology Physics, Jan. 1984, 297–305.

Mick Radio–Nuclear Instruments, Inc. Invoice 9398, Jul. 28, 1998.

* cited by examiner

Primary Examiner—Michael J. Hayes
Assistant Examiner—Catherine Serke
(74) Attorney, Agent, or Firm—Kenyon & Kenyon

(57) ABSTRACT

A template for surgically implanting needles into a patient's body. A support backing of the template specifically angled and curved to conform to a body structure to provide stability in the relative positions between the body and the template. The template further having a locking mechanism to hold needles in place after they have been inserted into the body structure, the locking mechanism utilizing a channel to guide a floating plate in vertical motion with respect to a contiguous stationary plate. When force is applied to the floating plate, the relative motion of the plates puts a locking force on the needles which run through holes in the two contiguous plates. A hollow protective covering to be mounted over the front face of the template to protect the ends of the needles that have been inserted through the template and into the patient.

18 Claims, 3 Drawing Sheets

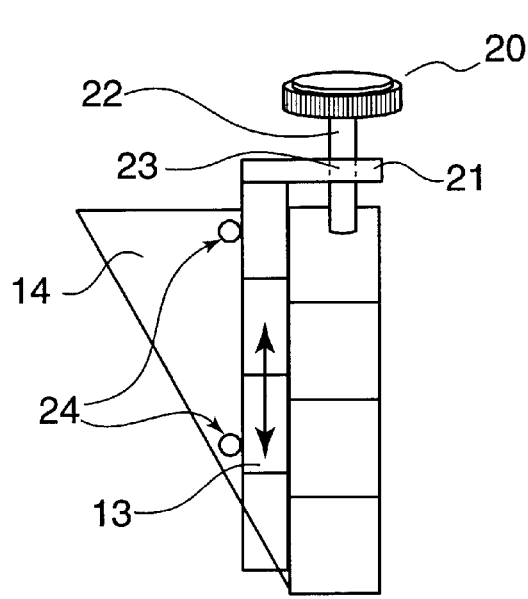
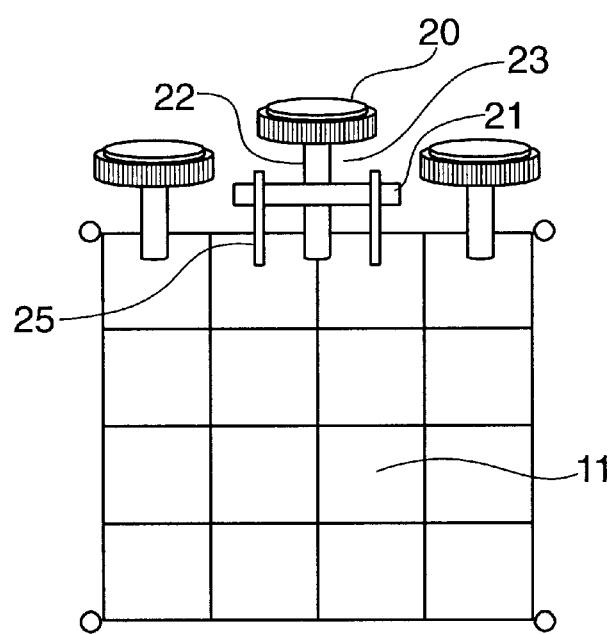
FIG. 2A
FIG. 2B

BRACHYTHERAPY NEEDLE IMPLANTATION TEMPLATE

FIELD OF THE INVENTION

The present invention relates generally to a template for the surgical implantation of needles into a patient's body, and more specifically to a template for implantation of needles for prostate brachytherapy.

BACKGROUND OF THE INVENTION

Various forms of cancer are treated by exposing cancerous tissues to controlled doses of radiation. One technique for delivering a dose of radiation to cancerous tissue is brachytherapy. Brachytherapy is a procedure that involves the implantation of radioactive sources in or near cancerous tissue in order to apply a desired dose of radiation. By implanting a radioactive source in or near targeted cancerous tissue, the desired radiation dose can be delivered, while limiting radiation exposure to other tissues. Brachytherapy which utilizes needles containing one or more radioactive sources to deliver the desired radiation dose into a patient is known to be an effective technique for treating prostate cancer.

In administering brachytherapy, a doctor will formulate a three dimensional dosimetry pattern for the placement of radioactive sources within a cancerous organ. In the seed implantation form of brachytherapy, radioactive "seeds" are discharged within the targeted cancerous organ via one or more hollow needles in accordance with the predetermined dosimetry pattern and these seeds are left inside the patient to deliver the desired radiation dosage. The implanted seeds are left within the patient to continue to deliver radiation even after the patient leaves the hospital. The level of radioactivity of the implanted seeds then gradually deteriorates until it becomes insignificant.

Another brachytherapy technique is to insert into and remove from a patient more intense radioactive sources in a timed pattern via hollow needles inserted into a target region. This technique, known as high dose rate brachytherapy ("HDR") delivers a desired dosage in a short amount of time, but avoids permanently implanting radioactive seeds. During an HDR treatment a timed pattern of intense radioactive sources are inserted and retracted through the needles over several minutes. This technique requires that the brachytherapy needles remain in the patient for many hours while a series of HDR treatments are administered.

For brachytherapy to have its desired effect it is important that a doctor be capable of precisely placing the brachytherapy needles into the patient. Needles are placed using a template which includes a grid of needle holes. Each needle hole on the grid may be uniquely identified by its own vertical and horizontal coordinates. It is intended that such a needle template be maintained at a constant position with respect to the patient's body surface and the cancerous organ. Thereby the preplanned dosimetry pattern may be implemented by inserting the needles through their designated coordinates on the template and into the patient.

In conjunction with a needle template, an ultrasound device is used to monitor the placement of the needles. In the case of prostate brachytherapy treatment, the ultrasound device is inserted into the rectum of the patient. During treatment, the needle template may be directly mounted on the ultrasound device to maintain a constant relative position between them. The needle template can also be sutured in place on the patient's body.

Once the needles have been inserted into the patient, it is desirable to provide a locking mechanism in the template to hold the needles in place so that the needle insertion depth will not change unintentionally. A conventional design for a locking mechanism is to make the template from a "sandwich" of three plates through which the needle holes extend. In this design, the outer and inner plates are fixedly positioned with respect to one an other and the middle plate moves slidably in a vertical direction between the two outer plates. Once the needles have been inserted through the template as desired, the needles are locked by turning a screw to apply vertical force to the middle plate thereby causing the middle plate to apply a vertical force to the needles in the template, preventing their unintentional movement.

For prostate brachytherapy, needles are inserted through the perineum of a patient to deliver a radioactive source to a cancerous prostate gland. To perform this procedure the patient is placed in the lithotomy position. The needle template is supported in a vertical upright position so that the needles may be inserted into the patient on a flat horizontal plane.

In attempting to maintain a constant position of the template relative to the patient during prostate brachytherapy, the template is sutured to the patient's skin in the perineum region. To support the template in place relative to the perineum, and to allow the sutures to be made, the template is rested in close contact with the surface of the perineum.

However, it is difficult to secure the known templates in place as these are generally square or rectangular and flat on the front and back surfaces. Flat templates are inconsistent with the shapes of patients' perineums.

In an attempt to address this problem, the gaps between the skin of the patient and the template have been stuffed with material such as gauze. However, such gauze stuffing is often irregular and can result in a cleanliness problem as the stuffing absorbs blood. Also, gauze stuffing may interfere with making a good suture of the template to the patient.

SUMMARY OF THE INVENTION

The present invention is directed to a brachytherapy needle template comprising an inclined and/or curved support backing conforming to a shape of a part of the patient's body. This support backing includes suturing eyelets which, when the device is in an operative position, are located adjacent to the patient's skin. This inclined and/or curved support backing allows the needle grid portion of the template to remain vertical when placed against the patient so that the needles may be inserted horizontally.

The present invention is further directed to a needle lock mechanism for holding the needles in place once they have been inserted into a patient. The needle lock mechanism comprises an arrangement of two plates, one of which moves slidably with respect to the other wherein the movable plate slides within a vertical channel formed, for example, by placing horizontal pins in a portion of the support backing. After the brachytherapy needles have been placed through the plates, a vertical force is placed on the movable plate and the force on the movable plate locks the needles in place.

BRIEF DESCRIPTION OF THE DRAWINGS

FIG. 2A shows a side view of the needle template according to the present invention illustrating the functionality of the locking mechanism;

FIG. 2B shows a front view of the needle template according to the present invention illustrating the functionality of the locking mechanism;

DETAILED DESCRIPTION OF THE INVENTION

Figure 1C:
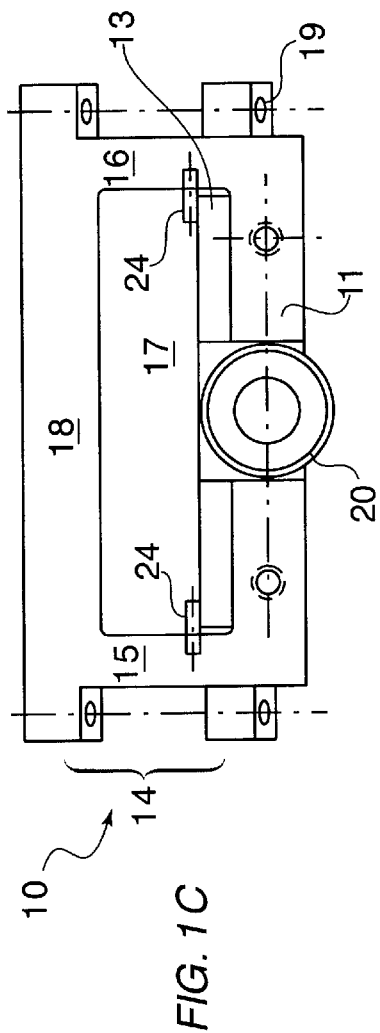
FIG. 1C shows a top view of a preferred embodiment of the needle template according to the present invention for use in prostate brachytherapy.
Figure 1A:
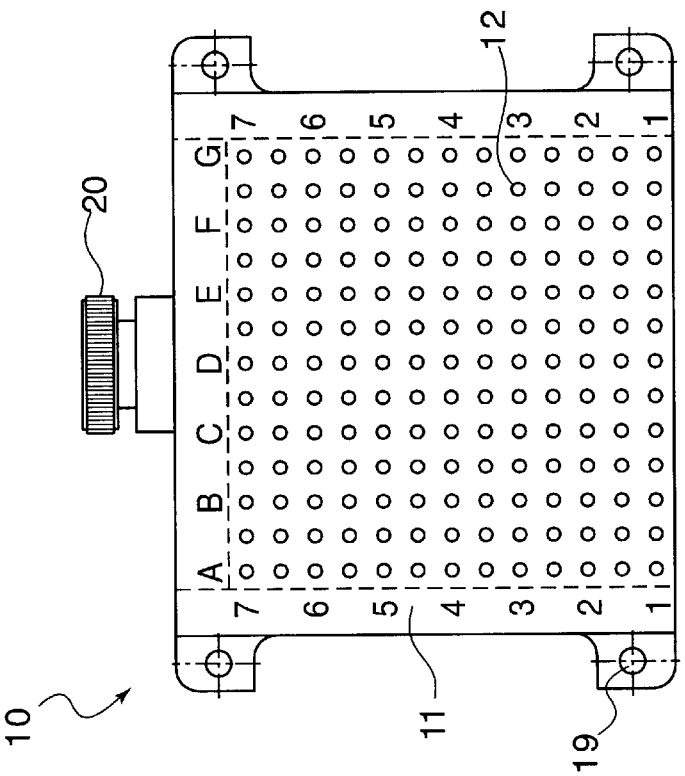
FIG. 1A shows a front view of a preferred embodiment of the needle template according to the present invention for use in prostate brachytherapy.
Figure 1B:
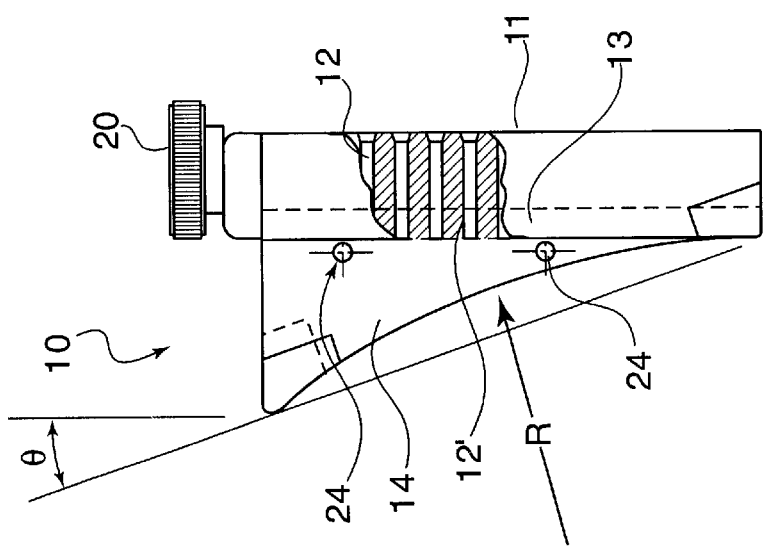
FIG. 1B shows a side view of a preferred embodiment of the needle template according to the present invention for use in prostate brachytherapy, including a partial cut away view of the plates and needle holes in the needle template.

FIGS. 1A–1C show a needle template 10 according to a preferred embodiment of the invention. FIG. 1A shows a substantially rectangular front plate 11 of the needle template 10. Needle holes 12, formed in a grid pattern, extend through the front plate 11 and a corresponding grid of needle holes 12' extends through a movable plate 13 received behind the front plate 11. Those skilled in the art will understand that the shape of the front plate 11 is unimportant so long as the desired number and location of needle holes 12 can be accommodated therein. The needle holes 12 and 12' are sized to accept brachytherapy needles (not shown), which typically range in size, for example, from 14 to 20 gauge.

when the grid patterns on the two plates 11 and 13 are aligned, brachytherapy needles can be inserted through the needle holes 12 in the front plate 11 and then through the holes 12' in the movable plate 13. As an end of a needle passes rearwardly from the movable plate 13, the end of the needle passes through gap 17, as seen in FIG. 1C, and passes from this gap into the patient. As will be explained in more detail below with respect to FIGS. 2A and 2B, by applying a vertical force to the movable plate 13, via lock knob 20, the movable plate 13 will be slightly moved upward with respect to the front plate 11, thereby applying a locking force to any needles inserted therethrough.

As shown in FIGS. 1B and 1C, front plate 11 is fixedly attached to support backing 14 which extends rearward from front plate 11. Support backing 14 extends rearwardly from plates 11 and 13, providing a frame for supporting and stabilizing plates 11 and 13 relative to a body part to be operated on. In a preferred embodiment of the invention, the front plate 11 and the support backing 14 may be integrally formed from a single piece of material. Support backing 14 extends rearwardly from the left and right edges of front plate 11 to form left and right rearward vertical supports 15 and 16. The rearward surfaces of the support backing 14, including rearward edges of the vertical supports 15 and 16, are shaped to conform to a body surface into which the needles are to be inserted.

As shown in FIG. 1B, for example, the rearward surfaces of support backing 14 are angled to account for a vertical and/or horizontal slope of the body part. For example, if the top portion of the body part is farther from plates 11 and 13 than the bottom portion, the top portion of the support backing 14 will preferably be formed extending rearward at an angle, θ, offset from the vertical in relation to a bottom portion of the support backing 14. Similarly if, when in a preferred position, a left portion of the body part is farther from the front plate 11 than a right portion, the left side of the support backing 14 would be extend rearward at an angle appropriate to offset the difference.

As shown in FIG. 1B, the rearward surfaces of support backing 14 are also curved, for example, as defined by a radius R, to correspond to a curvature of the body part against which it is to be seated. Of course, those skilled in the art will understand that, where a body part curves with respect to a vertical axis, the rear surfaces of support backing 14 may preferably be curved, for example, along a circle of radius R, to approximate this curve.

For a template embodiment used for prostate brachytherapy, as shown in FIGS. 1A–C, the support backing 14 includes both an angle and a curve so that the template 10 can rest stably and comfortably against the perineum. To rest stably against the perineum, an angle θ between the upper portion of support backing 14 and the vertical may, for example, be approximately 20 degrees. Angles θ, in the range of 5 to 45 degrees are also suitable for use in the prostate brachytherapy embodiment. A support backing 14 having a curvature with a radius of 4.55 inches is preferred. However, radii in the range of 3 to 6 inches are also suitable.

As shown in FIG. 1C, an open gap 17 extends between the left rearward vertical support 15 and the right rearward vertical support 16. This open gap 17 corresponds to a region in which the needles exit the movable plate 13 and then proceed rearwardly to enter the body. Gap 17 allows medical personnel to observe the entry of the needle into the body, and to make any necessary adjustments.

Also shown in FIG. 1C is a horizontal support component 18 of the backing support 14 which extends from the upper portion of left rearward vertical support 15 to the upper portion of right rearward vertical support 16. Horizontal support 18 adds additional surface area with which to maintain stability against the body part and allows viewing and access into the gap 17. The rear surface of horizontal support 18 may also preferably be angled and/or curved to conform to angles and curves of the portion of the body with which it is to be in contact.

For different applications of the present invention, other combinations of vertical supports 15, 16 and horizontal supports 18 may be employed to achieve the desired structure for a support backing 14.

As shown in FIGS. 1A–C, suture eyelets 19 are formed at a rearward corners of support backing 14. As with the rest of support backing 14, the rearward surfaces of eyelets 19 may also be angled and curved to correspond to a contour of the body. This angling and curvature of the suture eyelets 19, allows the suture eyelets 19 to be positioned in close proximity to the surface of the body part, thereby allowing the needle template 10 to be securely sutured to the patient.

Front plate 11, movable plate 13, and support backing 14 may preferably be manufactured from a strong but light material, such as, for example, aluminum or, more preferably, clear polycarbonate. Clear polycarbonate is strong and allows light to pass therethrough allowing medical personnel to more clearly see the needle insertion in the body. The clear polycarbonate may also be easily milled and drilled to form the structures discussed above. Also in a preferred embodiment, removing polycarbonate to hollow out structures such as the left and right rearward vertical supports 15 and 16 will reduce the weight of the device, reducing strain on the sutures attaching the needle template 10 to the patient.

FIGS. 2A and 2B show the locking mechanism of the invention which secures brachytherapy needles in place once they have been inserted into the patient. Specifically, the locking mechanism includes the fixed front plate 11, the movable plate 13, and needle holes 12 and 12' formed in their respective matrices. Thus, when the plates 11 and 13 are aligned, each needle may be passed through a first hole 12 in plate 11 and then through a corresponding hole 12' in plate 13. To lock the needles in place, pressure is applied to move the movable plate 13 a slight distance upward with respect to the front plate 11. This relative movement puts pressure on the needles extending through both the front plate 11 and the movable plate 13 and secures the needles in place. Those skilled in the art will understand that any directional displacement of the plate 13 to bring the grid of holes 12' out of alignment with the holes 12, will lock the needles in place. Thus, the plate 13 may be moved upward, downward, left, right, or in any combination of these directions to lock the needles in place.

In the preferred embodiment of the present invention, a lock knob 20 engage a tab 21 that extends from the top of the movable plate 13 above a top of the stationary front plate 11. The lock knob 20 turns a screw 22 engaged in a threaded hole 23 which extends through the lock knob tab 21. When the lock knob 20 is turned in a clockwise direction the screw 22 proceeds downward through the threaded hole 23 and comes into contact with the top of stationary front plate 11. When the screw 22 is turned while it is in contact with the top of the front plate 11, an upward force is applied to the floating plate 13 through the lock knob tab 21. To prevent excessive shear stress from damaging the needles, the locking screw 22 is preferably only long enough to move the floating plate 13 a distance sufficient to lock the needles without damaging them. Thus, the screw 22 becomes fully engaged in hole 23 and will not turn any more in the clockwise direction when the maximum desired lift has been attained. Preferably, to avoid damaging the needles, the lift of the movable plate 13 may be limited to approximately 10% of the gauge diameter of needle holes 12.

The movable plate 13 is held against the back of the stationary front plate 11 in a channel formed by channel pins 24 (also depicted in FIGS. 1B and 1C) extending horizontally from an inner surface of the support backing 14. For example, the channel pins 24 extend inward from left and right rearward vertical supports 15 and 16. The channel pins 24 may also be supported by any other structure which is fixedly attached to the stationary front plate 11. For example, it is possible to position the floating plate 12 in front of the plate 11 by extending a support structure forward from the plate 11, and positioning channel pins 24 there to form a channel for the floating plate 13.

In addition to the channel pins 24, two vertical tab pins 25 are positioned on top of the front plate 11 extending into corresponding vertical holes in the lock knob tab 21. These tab pins 25 are slidably engaged in the vertical holes in the lock knob tab 21, permitting vertical motion of the floating plate 13.

In the preferred embodiment, the lock knob 20, channel pins 24 and vertical tab pins 25 are made from stainless steel.

Figure 3A:
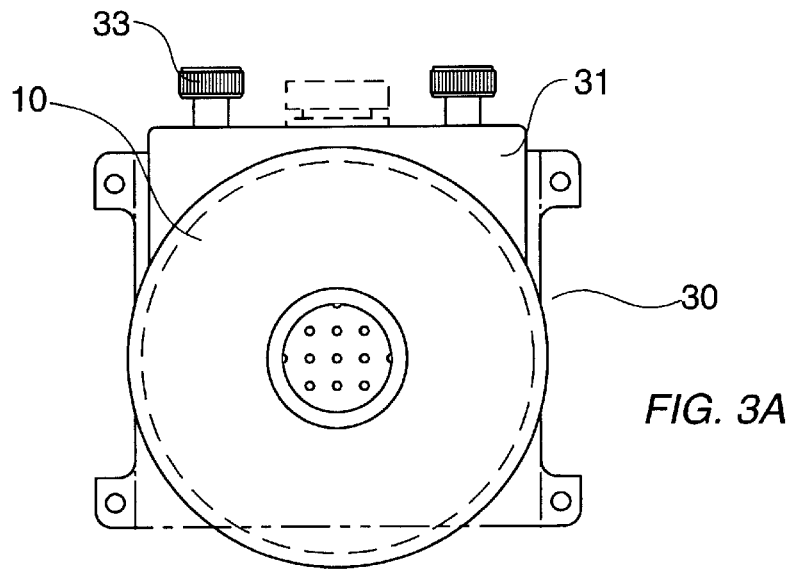
FIG. 3A shows a front view of a preferred embodiment of the protective covering attached to the face of the needle template according to the present invention.
Figure 3B:
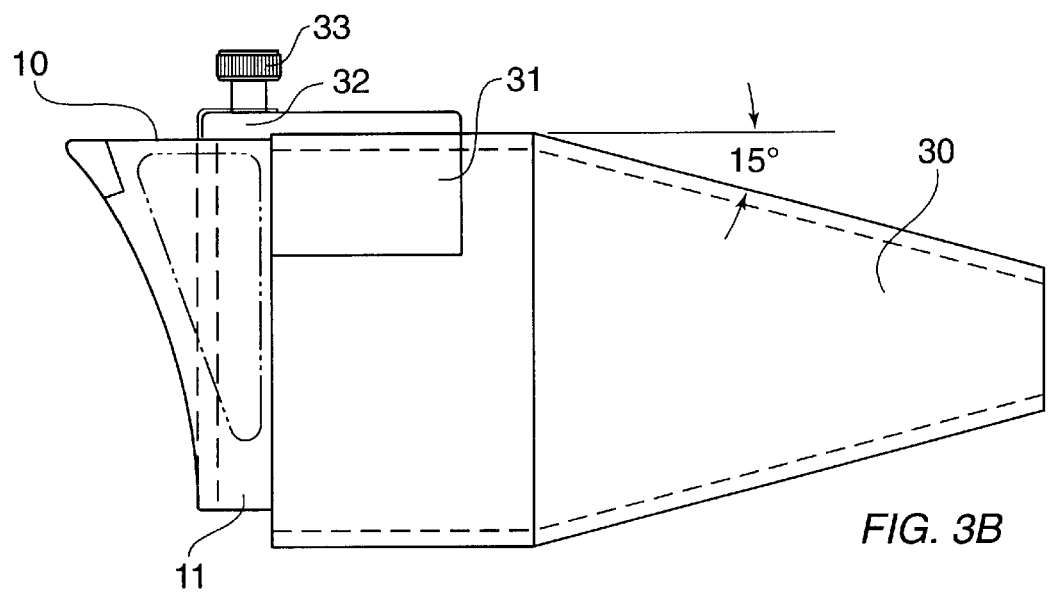
FIG. 3B shows a side view of a preferred embodiment of the protective covering attached to the face of the needle template according to the present invention.
Figure 3C:
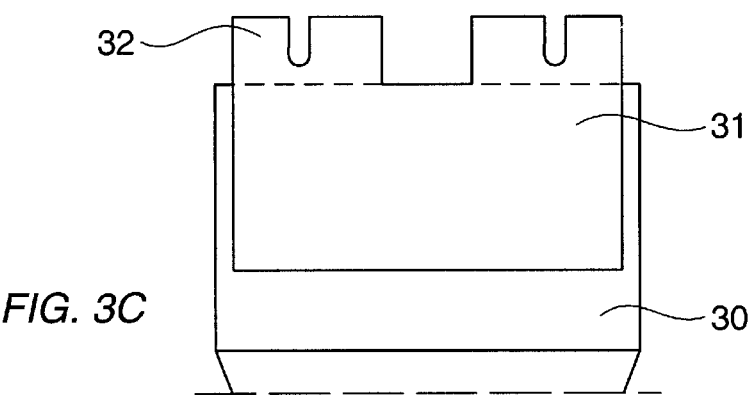
FIG. 3C shows a top view of a preferred embodiment of the attaching portion of the protective covering according to the present invention.

FIGS. 3A, 3B and 3C show a protective covering which further prevents the inadvertent movement of the needles once they have been inserted through the template 10 and into the patient. The protective covering 30 covers an outer face of the front plate 11 and extends outward to allow the ends of the brachytherapy needles to extend from the template 10. For use in brachytherapy, the protective covering 30 preferably extends approximately six inches out from the face of the front plate 11. A portion of the protective covering 30 adjacent to the template 10 may preferably be substantially cylindrical and may taper into a frustoconical shape as it extends outward therefrom. As shown in FIGS. 3A and 3B, an outward end of the frustoconical portion of the protective covering 30 may be open to a hollow interior thereof. This cylindrical and frustoconical design of the protective covering 30 provides protection for the needles without adding unnecessary edges or surfaces which may be inadvertently moved by a person or object. Other variations in the shape of the protective covering 30 will be apparent to those skilled in the art.

As shown in FIGS. 3A–3C, the protective covering 30 includes a mounting assembly 31 which includes slotted tabs 32 which extend rearwardly from the hollow conical portion of the protective covering 30. To mount the protective covering 30 on the template 10, the slotted tabs 32 are slid rearward to engage thumbscrews 33 which are mounted on the top of the front plate 11. Once the thumbscrews 33 are fully engaged by the slotted tabs 32, and the rear end of protective covering 30 is flush against the front plate 11, the thumbscrews 33 are tightened down on the slotted tabs 32 to hold the protective covering 30 in place.

The protective covering 30, including the mounting assembly 31, may, for example, be made from clear acrylic. For ease of manufacturing, in the preferred embodiment the mounting assembly 31 may be formed separately and later glued to the rest of the protective covering 30 using a suitable adhesive.

The protective covering 30 prevents inadvertent movement of the needles by the patient or hospital personnel. The protective covering 30 also serves to keep the needles clean and unobstructed. Protection of the needles is especially important during in HDR brachytherapy procedure where a radioactive source must be able to slide in and out of the needles in an unobstructed manner and where the needles must remain within the patient for an extended time.

There are many other variations of the above described embodiments which will be apparent to those skilled in the art. It is understood that these modifications are within the teaching of the present invention which is to be limited only by the claims appended hereto. In addition, although the operation of the preferred embodiments have been described in regard to prostate brachytherapy, those skilled in the art will understand that this invention may also be used to perform other types of treatments which require the accurate placement of needles into a patient.

What is claimed is:

1. A template for surgically inserting needles into a body, comprising:
   a first plate including a first plurality of first needle holes arranged in a predetermined grid pattern, the plate having a front side and a rear side;
   a support backing fixedly attached to the first plate, the support extending rearwardly from the first plate and defining a rear surface, the rear surface being angled relative to the first plate, the angle corresponding to an angle of a portion of the body against which the support backing is to be placed when the template is in a desired needle insertion position;

wherein the rear surface is curved to conform to a curvature of the portion of body.

2. The template as described in claim 1 wherein the support backing further comprises a plurality of suturing eyelets positioned adjacent to the rear surface.

3. The template as described in claim 2 wherein the body portion is a perineum, and wherein the device is in the desired needle insertion position with the body in a lithotomy position, the rear surface forms with respect to the vertical an angle between 5° and 45°, and the rear surface extending along a substantially circular curve have a radius between 3 and 6 inches.

4. The template as described in claim 3 wherein the angle is approximately 20° and the radius is approximately 4.6 inches.

5. A template for surgically inserting needles into a body comprising:
   a first plate including a first plurality of first needle holes arranged in a predetermined grid pattern, the plate having a front side and a rear side;
   a support backing fixedly attached to the first plate, the support extending rearwardly from the first plate and defining a rear surface, the rear surface being angled relative to the first plate, the angle corresponding to an angle of a portion of the body against which the support backing is to be placed when the template is in a desired needle insertion position; and
   a second plate having a plurality of second holes extending therethrough, the second holes being arranged in a pattern corresponding to the predetermined pattern of the first holes so that, when the first and second plates are in a predetermined alignment, each of the first holes aligns with a corresponding second hole;
   wherein the second plate is movably mounted so that the second plate may be moved into and out of the predetermined alignment with the first plate.

6. A lockable template for surgically inserting needles into a body structure comprising:
   a first plate including a plurality of first needle holes arranged in a predetermined pattern;
   a second plate including a plurality of second needle holes arranged in a pattern corresponding to the predetermined pattern of the first needle holes, the second plate being movable relative to the first plate, so that when the first and second plates are in a predetermined needle insertion position, the first and second needle holes align with one another;
   a support structure extending from the first plate;
   a channel for holding the second plate flat against the first plate, wherein the channel is formed by a channel pin supported on the support structure.

7. The locking template as described in claim 6 further comprising a means for moving the second plate in a predetermined direction.

8. The locking template as described in claim 7 wherein the means for moving the second plate comprises a locking screw engaged in the second plate and positioned to press against a surface of the first plate when the locking screw is turned.

9. The locking template as described in claim 8 wherein the locking screw is limited in length to prevent the second plate from being moved more than a distance of 10% of a gauge diameter of the first and second needle holes from the needle insertion position when the locking screw is tightened.

10. The locking template as described in claim 10 wherein the predetermined direction is an upward vertical direction.

11. The locking template as described in claim 6 wherein the support structure forms a support backing and wherein the channel pin is supported on the support backing.

12. The locking template as described in claim 6, further comprising an arrangement configured to move the second plate in a predetermined direction.

13. The locking template as described in claim 12, wherein the arrangement includes a locking screw engaged in the second plate and configured to press against a surface of the first plate when the locking screw is turned.

14. The locking template as described in claim 13, wherein the locking screw is limited in length to prevent the second plate from being moved more than a distance of 10% of a gauge diameter of the first and second needle holes from the needle insertion position when the locking screw is tightened.

15. The locking template as described in claim 12, wherein the predetermined direction is an upward direction.

16. A template for surgically inserting needles into a body comprising:
   a plate including a plurality of needle holes arranged in a predetermined pattern, the plate having a needle insertion side facing away from the body when the template is in a needle insertion position;
   a protective covering selectively coupleable to the needle insertion side of the plate, the protective covering having a hollow interior with a majority of the needle holes received in the hollow interior.

17. The template as described in claim 16 wherein a portion of the protective covering mountable to the needle insertion side is substantially cylindrical, the protective covering extending away from the needle insertion side in a substantially conical shape decreasing in diameter.

18. The template as described in claim 16 wherein the plate further comprises a thumb screw on a surface of the plate, the protective covering further comprising a slotted tab aligned to engage the thumb screw and being secured to the plate when the thumb screw is tightened while the slotted tab is engaged with the thumb screw.

* * * * *